United States Patent [19]
Goble et al.

[11] Patent Number: 5,851,219
[45] Date of Patent: Dec. 22, 1998

[54] SUTURE ANCHOR ASSEMBLY

[75] Inventors: E. Marlowe Goble; Alan Chervitz; David P. Luman; Kenneth L. Jensen, all of Logan, Utah

[73] Assignee: Mitek Surgical Products, Inc., Westwood, Mass.

[21] Appl. No.: 960,936

[22] Filed: Oct. 30, 1997

Related U.S. Application Data

[63] Continuation of Ser. No. 393,553, Feb. 23, 1995, abandoned.

[51] Int. Cl.$^6$ ........................................................ A61B 17/04
[52] U.S. Cl. .................................. 606/232; 606/72; 606/73
[58] Field of Search .................................. 606/232, 72, 73

[56] References Cited

U.S. PATENT DOCUMENTS 4,537,185   8/1985   Stednitz .
5,141,520   8/1992   Goble et al. .............................. 606/232
5,607,432   3/1997   Fucci ........................................ 606/232

*Primary Examiner*—Michael Buiz
*Assistant Examiner*—Daphja Shai
*Attorney, Agent, or Firm*—Pandiscio & Pandiscio

[57] ABSTRACT

There is presented a suture anchor comprising a head portion and a connector portion. The head portion includes a pointed free end, a cutting flute extending substantially throughout the length of the head portion, and screw threads extending substantially throughout the length of the head portion. The connector portion extends axially from the head portion for releasable connection to an anchor inserter. The connector portion is provided with structure for attachment of a suture thereto. There is further presented a suture anchor inserter for use in combination with the suture anchor in attachment of the anchor to a bone, and a suture anchor length of suture material. There is still further presented a method for anchoring a length of suture to a bone.

7 Claims, 4 Drawing Sheets

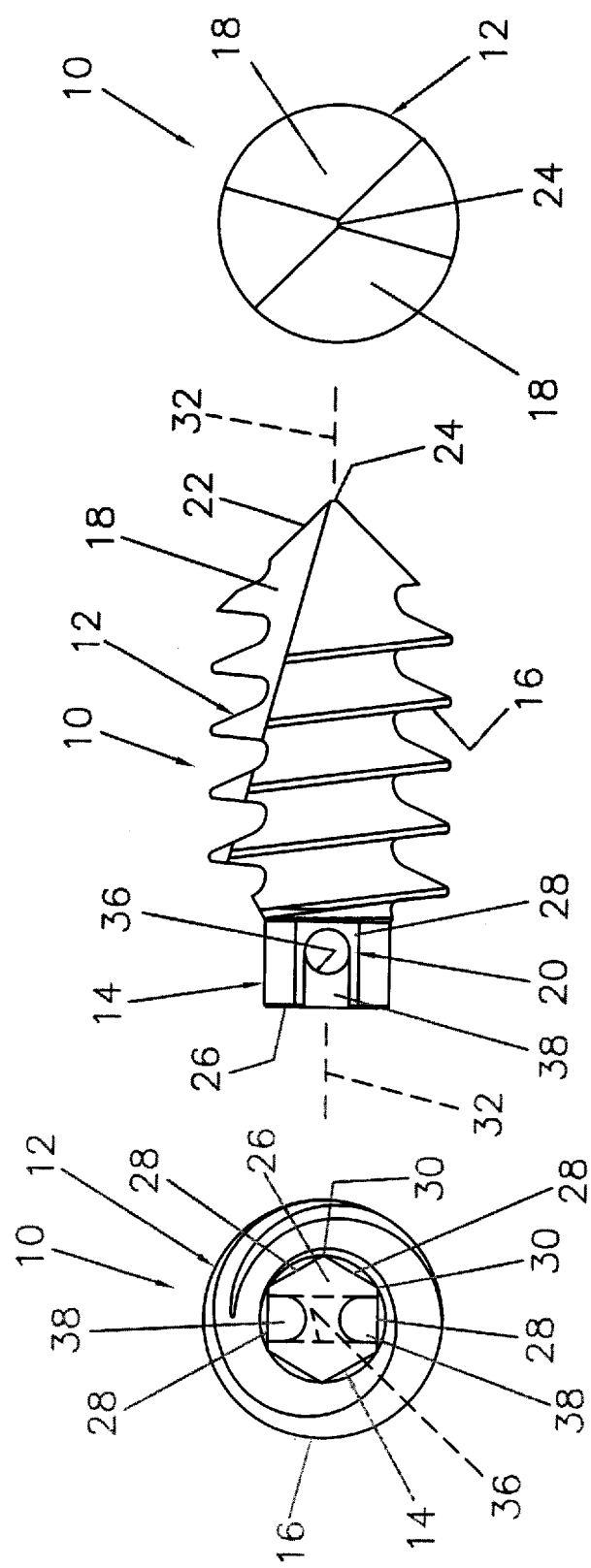

SUTURE ANCHOR ASSEMBLY

This application is a continuation of application Ser. No. 08/393,553 filed on Feb. 23, 1995 now abandoned.

FIELD OF THE INVENTION

The present invention relates generally to devices for attaching suture to bone, and more particularly to such devices that are self-tapping.

BACKGROUND OF THE INVENTION

Self-tapping suture anchors are well known in the art. See, for example, U.S. Pat. No. 4,632,100, issued Dec. 30, 1986 to Somers et al., which discloses a cylindrical suture anchor having a drill portion formed at one end and flights of threads formed at the other end. A length of suture is fixedly attached to the suture anchor so as to extend therefrom. The suture anchor may be turned, and hence deployed into a target bone, by means of a driver that matingly engages the anchor by means of a splined coupling, with the free end of the suture being stored within the body of the driver. In practice, the drill end of the suture anchor is positioned against the target bone and the suture anchor is turned by means of the driver, causing the drill portion of the suture anchor to cut into the bone. As the drill portion of the suture anchor cuts into the bone, thus forming a hole therein, the suture anchor threads engage the inner surface of the hole. The leading thread flights tap the hole so as to provide a seat for the following thread flights. In due course, the anchor separates from the driver, with the stored suture paying out from the interior of the driver.

Unfortunately, while suture anchors of the type taught by Somers et al. generally perform well, they are not completely satisfactory for all surgical procedures in which suture must be attached to bone. In particular, with the suture anchor of Somers et al., the suture is attached to the anchor by fastening the suture to a disc, which is then fixed in position within a blind hole formed in the proximal end of the anchor. Unfortunately, this arrangement can be cumbersome, particularly where the anchor is to be formed with a relatively small size. Furthermore, with the suture anchor of Somers et al., the splined coupling used to connect the driver to the anchor comprises a polygonally-shaped male portion on the driver and a corresponding polygonally-shaped female portion on the anchor. This construction can present a constraint on depth of thread, particularly where it is desired to form the anchor in a relatively small size. Moreover, with the suture anchor of Somers et al., the anchor's drill portion terminates intermediate the anchor's length. Accordingly, excised bone matter can sometimes build up in front of, and to the side of, the deploying anchor, thereby possibly impeding efficient deployment of the anchor. Also, with the suture anchor of Somers et al., the anchor's thread flights are formed along only a portion of the anchor's body. This construction can present a constraint on the anchor's holding power, particularly where it is desired to form the anchor in a relatively small size. In addition, with the suture anchor of Somers et al., the length of suture is fixedly connected to the suture anchor. This can present a problem for some applications, e.g. arthroscopic procedures, where it may be desirable to have the suture capable of sliding relative to the anchor so as to facilitate knot rundown techniques.

OBJECTS OF THE INVENTION

Accordingly, an object of the present invention is to provide a suture anchor comprising drill means, screw thread means, and suture attachment means, all formed in a unitary anchor body.

Another object of the present invention is to provide a suture anchor having a male polygonally-shaped proximal connector portion adapted to be received by, and readily released by, a corresponding polygonally-shaped recess formed in a suture anchor inserter socket portion.

Still another object of the present invention is to provide a suture anchor wherein flights of screw threads extend along substantially the entire length of the anchor, less the connector portion of the anchor, and drilling flutes extend along substantially the entire length of the anchor, less the connector portion of the anchor.

Yet another object of the present invention is to provide a suture anchor of solid construction permitting deeper screw threads therein.

A still further object of the present invention is to provide a suture anchor assembly having a reduced manufacturing cost.

Yet another object is to provide a suture anchor wherein the suture attachment means will permit the attached suture to be slidable relative to the deployed anchor.

And another object of the present invention is to provide an inserter for use in combination with the aforementioned anchor.

Still another object of the present invention is to provide a suture anchor assembly featuring the aforementioned anchor and inserter in combination with a length of suture.

Yet another object of the present invention is to provide an improved method for anchoring suture in bone.

SUMMARY OF THE INVENTION

With the above and other objects in view, as will hereinafter appear, a feature of the present invention is the provision of a suture anchor comprising a unitary anchor body having therein drill means, screw thread means, connector means for connection of the anchor to an anchor inserter, and suture attachment means. The drill means and screw thread means are disposed on a head portion of the anchor and are adapted to penetrate the bone when the anchor is pressed against the bone and the anchor is rotated about its longitudinal axis. The drill means and the screw thread means extend along substantially the entire length of the head portion of the anchor and are adapted to deploy the anchor into the bone when the anchor is rotated. A proximal portion of the anchor body comprises a connector portion that terminates in a proximal end surface. The connector portion of the anchor is adapted to be received in the distal end of an inserter prior to insertion of the suture anchor into a bone. The suture attachment means are disposed in the connector portion of the anchor and are adapted to permit a length of suture to be attached to the anchor.

In accordance with a further feature of the invention, the drill means comprise a pointed distal end and at least one cutting flute that extends from the distal end of the anchor to adjacent the connector portion. The screw thread means comprise a single, continuous thread that extends from the anchor distal end to adjacent the anchor connector portion. The connector portion of the anchor is a polygonal configuration in cross-section. The suture attachment means comprise a bore through the connector portion of the anchor, and a pair of channels extending between two ends of the bore and the proximal end surface of the connector portion. The channels are adapted to receive a portion of a length of suture so as to: (i) recess the suture within the anchor connector portion so that the suture will not interfere with the connector portion of the anchor being received in the inserter; (ii) allow for sliding movement of the suture relative to the connector portion of the anchor once the suture anchor has been installed in the bone; and (iii) recess the suture within the connector portion so as to protect the suture from abrasion during anchor deployment and after anchor seating.

The foregoing suture anchor is intended to be installed in a bone using an inserter. In accordance with a further feature of the present invention, there is provided an inserter comprising a tubular shaft and a tubular shaft tip. The tubular shaft tip is joined to a distal end of the tubular shaft, and has therein a polygonally-shaped recess extending axially into its distal end. The polygonally-shaped recess is adapted to matingly receive the polygonally-shaped connector portion of the suture anchor, whereby the suture anchor can be rotated about its longitudinal axis using the inserter. The tubular shaft further comprises means for controlling and storing one or more lengths of suture extending from the connector portion of the anchor.

In accordance with a further feature of the present invention, there is provided a suture anchor assembly including the above-described suture anchor and inserter, and in combination therewith, a length of suture attached to the connector portion of the anchor.

In accordance with a still further feature of the present invention, there is provided a method for anchoring suture in bone, the method comprising the steps of:

providing an anchor having a head portion and a connector portion, the head portion having a pointed free end, a cutting flute extending from the pointed free end to adjacent the connector portion, and screw threads extending from the pointed free end to adjacent the connector portion, the connector portion extending axially from an end of the head portion spaced from the pointed free end of the head portion and having therein suture attachment structure, wherein the anchor has a length of suture attached to the anchor connector portion and extending into an inserter, with the anchor and inserter being drivingly interconnected to one another;

attaching a power rotary means to the inserter;

pressing the pointed free end of the anchor against a bone;

rotating the anchor such that the anchor pointed end, cutting flute and screw threads operate to move the anchor into the bone;

releasing the anchor from the inserter upon the movement of the anchor into the bone beyond a free end of the inserter; and removing the inserter from the bone and paying out the suture length from the inserter.

The above and other features of the invention, including various details of construction and combinations of parts and steps, will now be more particularly described with reference to the accompanying drawings and pointed out in the claims. It will be understood that the particular devices and method embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings:

FIG. 1 is a side elevational view of a suture anchor of an illustrative embodiment of the invention;

FIG. 2 is a rear elevational view of the suture anchor shown in FIG. 1, with the anchor having been rotated 90° about its longitudinal axis from the position shown in FIG. 1;

FIG. 3 is a front elevational view of the suture anchor shown in FIG. 1, with the anchor having been rotated 90° about its longitudinal axis from the position shown in FIG. 1;

DESCRIPTION OF THE PREFERRED EMBODIMENTS

Figure 4:
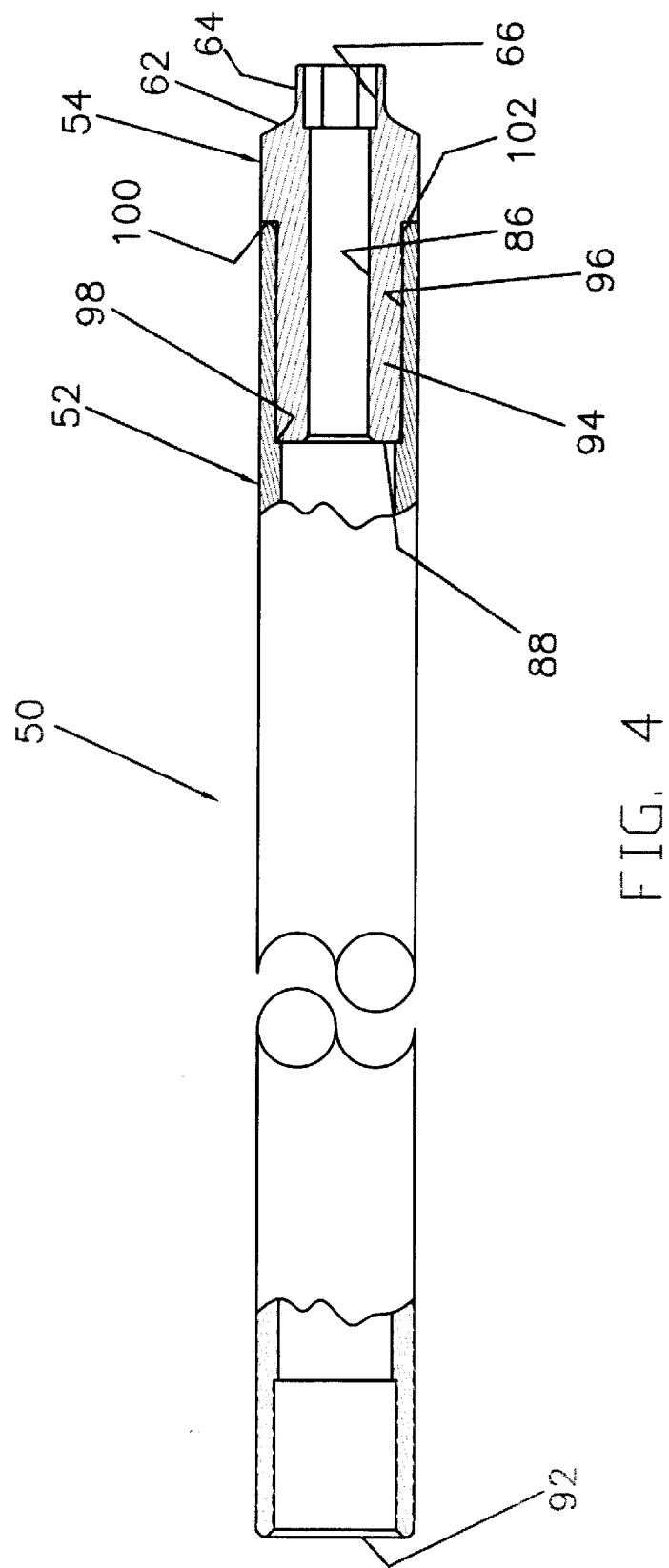
FIG. 4 is a side elevational view, partially broken away and partially in section, showing one form of inserter illustrative of an embodiment of the invention and suitable for use with the anchor of FIGS. 1–3.

Referring to FIG. 1, it will be seen that an illustrative suture anchor includes a unitary body 10 having a head portion 12, a connector portion 14, a continuous screw thread 16, at least one cutting flute 18, and suture attachment means 20. Suture anchor body 10 may be formed from any of the various biocompatible or bioabsorbable materials known in the art. In a preferred embodiment, the suture anchor body 10 is formed of surgical grade titanium alloy.

The suture anchor head portion 12 includes, at a free end 22 thereof, a distal point 24. In a preferred embodiment, the head portion 12 is of a generally cylindrical configuration. Alternatively, head portion 12 may be of other configurations without departing from the scope of the invention.

The connector portion 14 includes an end surface 26 (FIGS. 1, 2 and 5) that is spaced from head portion 12. The connector portion 14 has a generally polygonal cross-section (FIG. 2). More particularly, the connector portion 14 comprises a multi-faceted profile that includes a plurality of flat sides 28 separated by a plurality of corners 30. In a preferred embodiment, the connector portion 14 is of hexagonal cross-section. Alternatively, other multi-faceted cross-sections may be used.

As may be seen in FIG. 1, the continuous screw thread 16 extends from the anchor free end 22 to the anchor connector portion 14. Because the anchor connector portion 14 is removed from the head portion 12 and comprises a male connector means, rather than a female connector means as shown in the aforementioned patent to Somers et al., the anchor head portion 12 is solid and devoid of any recess internally thereof. Such construction permits deeper screw threads to be cut in the anchor head portion. While the deepness of the screw threads will vary with the size of the anchor, the threads are substantially deeper than are permitted by constructions such as shown in the aforementioned patent to Somers et al. The use of screw threads which extend substantially throughout the length of the anchor head portion and which extend more deeply into the anchor head portion provides for a more secure lodgement of the anchor in bone.

Referring again to FIG. 1, it will be seen that at least one cutting flute 18 extends from distal point 24, along substantially the entire length of the anchor head portion 12. Preferably, two cutting flutes 18 are provided (FIG. 3). Each flute 18 is sized and shaped so as to aggressively remove enough bone during each revolution of the anchor body 10 to allow each flight of thread 16 to advance forward into the target bone. In this respect, it will be understood that the rate at which the anchor 10 advances into the bone with each revolution is determined by the pitch of the thread 16.

In a preferred embodiment, each flute 18 forms an angle with the anchor's longitudinal axis 32 in the range of from about 150° to about 250°, with a preferred angle of about 200°. Each flute 18 also forms a transverse included angle on anchor body 10 in the range of from about 115° to about 125°, with a preferred angle of about 120°.

As best seen in FIGS. 1 and 2, the suture attachment means 20 comprise a bore 36 which extends transversely through the anchor connector portion 14. The bore 36 is disposed so as to be centered on two diametrically-opposing flat sides 28 of the connector portion 14 (FIGS. 1 and 2). A pair of channels 38 extend proximally from, and communicate with, the two ends of the bore 36. The channels 38 open on the anchor's connector portion end surface 26 and provide clearance for a suture 40 (FIG. 5) to pass between (i) the suture anchor body 10 and the adjacent inserter structure when the suture anchor is seated in an associated inserter, as will hereinafter be disclosed in further detail, and (ii) the suture anchor body 10 and the adjacent bone, after the suture anchor body 10 has been installed in the bone, as will hereinafter be disclosed in further detail. In addition, the bore 36 and channels 38 are sized so that the suture 40 can slide freely relative to the suture anchor 10 once the suture anchor has been installed in a bone.

Figure 5:
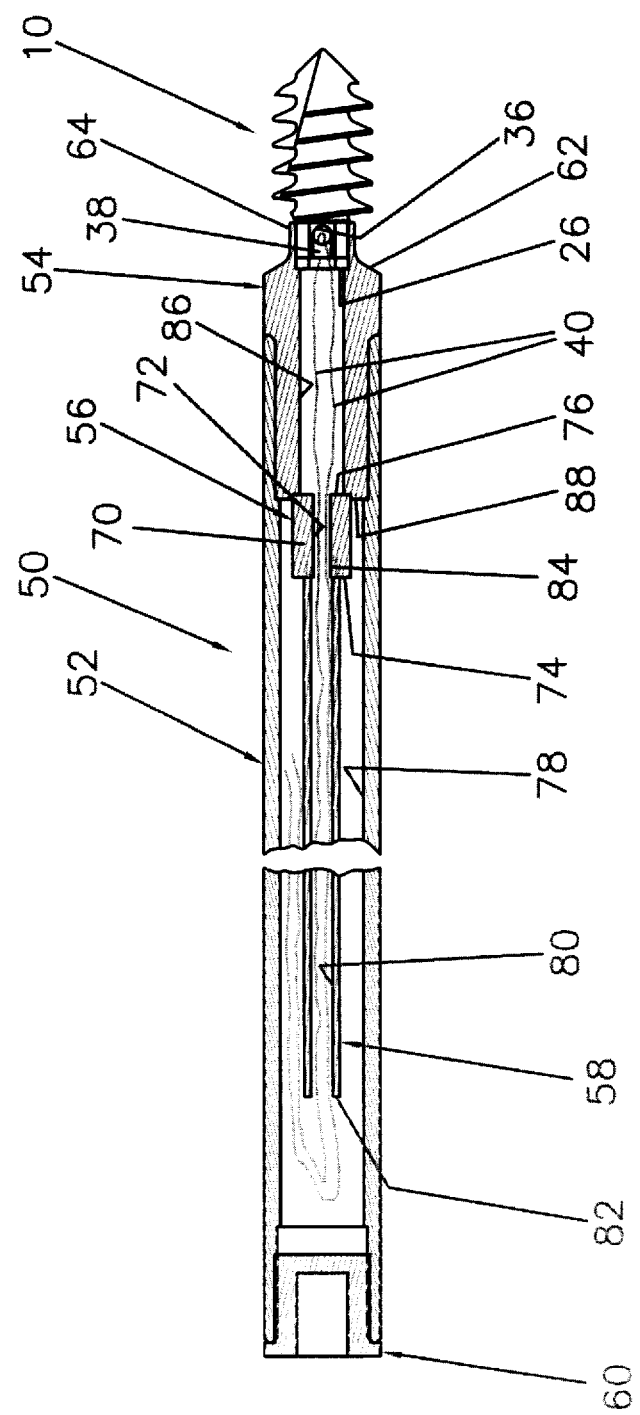
FIG. 5 is a side elevational view of one form of suture anchor assembly, illustrative of an embodiment of the invention, the assembly including the anchor of FIG. 1 in combination with the inserter of FIG. 4, the inserter shown in section.

The suture anchor 10 is intended to be installed in a bone by means of an inserter 50. Referring to FIGS. 4 and 5, the inserter 50 comprises a tubular shaft 52, a tubular shaft tip 54, a suture gripper 56 (FIG. 5), a suture sleeve 58, and a cap 60. In a preferred embodiment, the inserter 50 is formed from any of the various biocompatible metal and/or polymer materials known in the art.

Referring still to FIGS. 4 and 5, tubular shaft tip 54 includes a generally frusto-conical annular shoulder portion 62 joining a socket portion 64 provided with a recess 66 of polygonal cross-sectional configuration. The polygonal cross-sectional configuration of the recess 66 of the socket portion 64 is complementary to the polygonal cross-sectional configuration of the connector portion 14 of the anchor body 10. As a result, the connector portion of the anchor body 10 is drivingly received in the shaft tip socket portion 64.

Referring to FIG. 5, it will be seen that the suture gripper 56 comprises a cylindrical body 70 having an internal passageway 72 that communicates between end surfaces 74 and 76. The suture gripper 56 preferably is of an elastomeric material, and is sized and shaped to fit loosely within a central passageway 78 of the tubular shaft 52. Internal passageway 72 of the suture gripper 56 is sized and shaped to snugly receive and thereby control the suture 40 when the anchor body 10 is fully assembled to the inserter 50, as will hereinafter be disclosed in further detail.

The suture sleeve 58 is provided with a central passageway 80 extending between ends 82, 84 thereof. The suture sleeve 58 is adapted to loosely receive the suture 40 when the anchor 10 is fully assembled to the inserter 50, as will hereinafter be disclosed in further detail. Suture sleeve 58 is sized so that an annular gap will be formed between (i) the outer surface of suture sleeve 58 and (ii) the inner surface of tubular shaft 52, when suture sleeve 58 is disposed within tubular shaft 52, as shown in FIG. 5.

Suture anchor body 10, suture 40, and inserter 50 are preferably assembled in the following manner. First, the tubular shaft tip 54 is assembled to the tubular shaft 52. This is done by aligning the tubular shaft tip 54 with the tubular shaft 52 and moving the tubular shaft tip 54 toward the tubular shaft 52 so that a tubular shaft tip cylindrical portion 94 enters a tubular shaft counterbore 96 (FIG. 4). The tubular shaft tip 54 is advanced into the counterbore 96 until the tubular shaft tip proximal end surface 88 engages a tubular shaft annular shoulder 98. As this occurs, a shoulder 100 of the tubular shaft tip engages a distal end 102 of the tubular shaft 52. Next, the suture 40 is drawn through the bore 36 of the anchor body 10 and pulled back so that the suture 40 lies within the channels 38. In this position, suture 40 extends leftwardly, as viewed in FIG. 1, from the connector portion end surface 26. Next, the free ends of the suture 40 are passed through recess 66 of the socket portion 64, through the central passageway 86 of the tubular shaft tip 54, and through the central passageway 78 of the tubular shaft 52 until the suture 40 exits an open proximal end 92 (FIG. 4) of the tubular shaft 52.

Once the free suture ends have been successfully threaded through the preceding parts, the anchor body 10 is inserted into the socket portion 64 of tubular shaft tip 54. The anchor 10 is oriented so that the flat sides 28 and corners 30 of the anchor connector portion 14 are aligned with their corresponding counterparts in the socket portion 64. The anchor 10 is then moved toward the tubular shaft tip 54 until the connector portion 14 is fully seated within the socket portion 64 of tubular shaft tip 54. In this respect, it will be understood that the relative dimensions of the anchor connector portion 14 and the tubular shaft tip 54 are selected such that a driving engagement will be maintained between the anchor 10 and the tubular shaft tip 54. At the same time, channels 38 provide pathways for the suture to pass into the central passageway 86 of tubular shaft tip 54.

Once the anchor 10 is securely positioned within the tubular shaft tip 54, the suture 40 is pulled taut. The suture gripper 56 is then slid over the suture 40 by passing the suture 40 through the suture gripper internal passageway 72. The suture gripper 56 is then inserted into the open proximal end 92 of the tubular shaft central passageway 78 (FIG. 5) and slid within the tubular shaft central passageway 78 until the suture gripper 56 abuts the tubular shaft tip proximal end surface 88. By keeping suture 40 taut as the suture gripper 56 engages end surface 88 of the tubular shaft tip 54, the suture gripper's gripping engagement with suture 40 will help keep anchor 10 mounted to tubular shaft tip 54.

The free ends of the suture 40 are then passed through the suture sleeve 58 via the central passageway 80. The suture sleeve 58 is then, in turn, inserted into the tubular shaft 52. The suture sleeve 58 is slid distally along the tubular shaft central passageway 78 until the suture sleeve distal end 84 engages the suture gripper 56. The free ends of the suture 40 are then inserted into the annular gap formed between the outer surface of suture sleeve 58 and the inner surface of tubular shaft 52.

Tubular shaft 52 is then closed off by inserting the cap 60 (FIG. 5) into the tubular shaft open proximal end 92 (FIG. 4).

Figure 6:
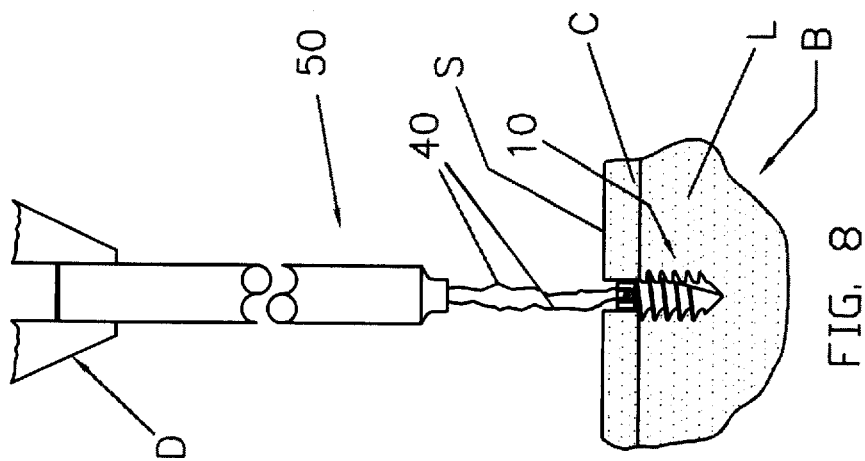
FIG. 6 is a diagrammatic view, showing the suture anchor assembly after a pointed distal end of the suture anchor has penetrated a cortical layer of bone.
Figure 7:
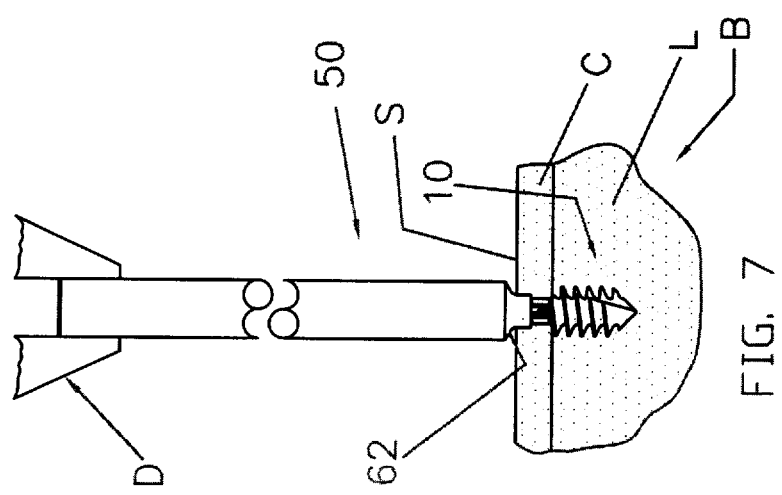
FIG. 7 is a view similar to FIG. 6, but showing the suture anchor assembly after the suture anchor has fully penetrated the bone and the anchor is separating from the inserter.
Figure 8:
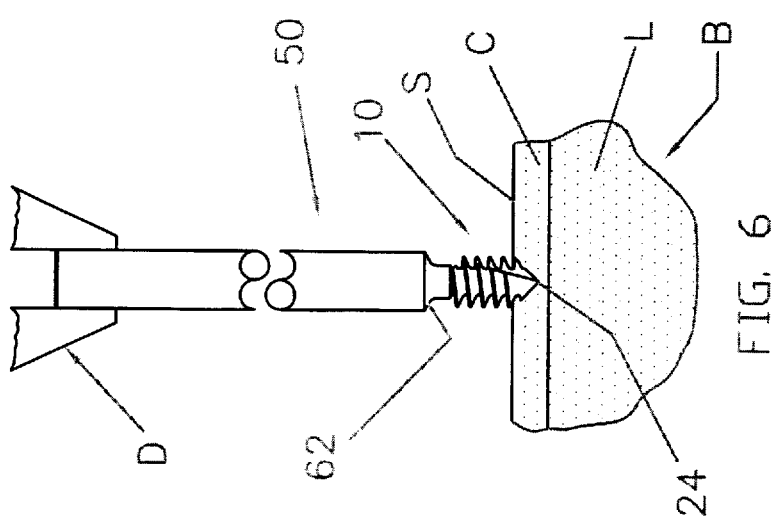
FIG. 8 is a view similar to FIGS. 6 and 7, but showing the suture anchor assembly after the suture anchor has been freed from the inserter, and showing the inserter withdrawn from the surface of the bone and the suture paying out therefrom.

In operation, and looking now at FIGS. 6–8, the above-described suture anchor assembly is assembled to a drilling means D of the sort well known in the art, such as to the chuck of a typical rotary drill. Once assembled to drilling means D, the suture anchor assembly is oriented such that the suture anchor 10 is positioned above a cortical bone layer C, with the distal point 24 resting on a top surfaces of a bone B. Once in this position, drilling means D is actuated and the anchor 10 is caused to rotate. As this happens, distal point 24 penetrates top surface S of bone B until the flutes 18 begin to cut away a portion of the cortical bone layer C. During this operation, axial pressure is applied to the drilling means D, so as to cause ever increasing portions of the cortical bone layer C to be cut away by the flutes 18. It will be understood that the amount of bone material removed by the combination of the distal point 24 and the cutting flutes 18 is directly related to the pitch and physical arrangement of the screw thread 16.

Once the distal point 24 and cutting flutes 18 have penetrated into a portion of the cortical bone layer C, the thread 16 begins to engage the hole formed by the cutting flutes 18. In this way, the thread 16 taps the inner surface of the hole so as to allow succeeding flights of thread 16 to securely engage the cortical bone layer C.

As seen in FIG. 7, once the suture anchor 10 has penetrated the cortical bone layer C and begins to cut into cancellous bone material L, the frusto-conical shoulder portion 62 of the tubular shaft tip 54 engages the top surface S of the bone B. As this happens, drill means D continue to rotate the anchor body 10, and the screw thread 16 continues to engage the tapped inner surface of the hole being formed in the bone B. Thus, the anchor body 10 is drawn further into the bone B even as forward progress of inserter 50 is inhibited by engagement of shoulder portion 62 with bone top surface S.

As the anchor is drawn further into the cancellous bone layer L, the anchor body 10 exits from its position within the tubular shaft tip 54. As this occurs, suture gripper 56 permits suture 40 to be pulled from the inserter by the separating anchor 10. Once the anchor 10 is released completely from the tubular shaft tip 54, driving of the anchor ceases and the inserter 50 is withdrawn from the surface S of the bone (FIG. 8), with suture 40 paying out from inserter 50. The suture 40 is then completely withdrawn through the suture sleeve 58 and suture gripper 56 until the free ends of suture 40 are pulled from tubular shaft tip 54.

It is to be appreciated that as the bone anchor is deployed into bone, the bone matter excised by flutes 18 can pass easily by the anchor by virtue of the fact that flutes 18 extend along substantially the entire length of anchor head portion 12. Thus, forward progress of the suture anchor into the bone is facilitated.

There is thus provided a suture anchor which includes drill means, screw thread means, and suture attachment means formed as a unitary anchor body, and wherein the suture anchor and an anchor inserter have complementary connector means readily releasable upon completion of an anchor positioning operation. There is further provided a suture anchor wherein both the drill means and the screw threads thereon extend substantially throughout the length of the anchor, less the connector means, and the anchor is adapted to securely engage bone. There is further provided an anchor of solid construction, having no internal recess therein, permitting the screw threads to be cut more deeply into the anchor body. There is still further provided a suture anchor having a lesser manufacturing cost than prior art anchors.

There is thus further provided an inserter for use with the above-described anchor, and a suture anchor assembly featuring the anchor, the inserter, and a length of suture material.

There is thus still further provided a method for anchoring suture in a bone.

It is to be understood that the present invention is by no means limited to the particular construction herein disclosed and/or shown in the drawings, but also comprises any modifications or equivalents within the scope of the claims.

What is claimed is:

1. A suture anchor comprising:
   a head portion having
      a generally conically-shaped and pointed distal end portion with opposed flutes cut therethrough; and
      screw threads extending from a proximal end of said conically-shaped distal end portion and substantially throughout an entire remainder of said head portion;
      said flutes each cutting through said remainder of said head portion and interrupting opposed portions of said screw threads;
      said flutes each cutting through said head portion inwardly removed from distal-most of said threads; and
      said flutes each cutting through a plurality of proximal-most of said threads between inner and outer diameters of said plurality of proximal-most threads;
      bottoms of said flutes diverging outwardly from said pointed distal end as said flutes extend proximally; and
   a connector portion extending proximally from said head portion, said connector portion comprising
      a plurality of planar sides extending throughout the length of said connector portion and terminating at an anchor proximal end surface, and defining the entire side surface of said connector portion;
      said connector portion defining a bore therethrough extending from one of said planar sides to an opposed one of said planar sides, said bore being adapted to receive a suture therethrough; and
      opposed channels extending from said anchor proximal end surface, through said one planar side and said opposed one of said planar sides, respectively, to respective opposite ends of said bore, said channels being adapted to receive the suture such that the suture does not extend outwardly beyond said one planar side and said opposed one planar side.

2. A suture anchor according to claim 1 wherein said bore is spaced from said flutes and said screw threads.

3. A suture anchor according to claim 2 wherein said head portion of said anchor is devoid of an internal recess, such that said screw threads extend from a solid central portion of said head portion.

4. A suture anchor according to claim 1 wherein said channels are adapted to receive a portion of said length of suture so as to: (i) recess said suture within said connector portion so that said suture will not interfere with the receipt of said connector portion by a suture anchor inserter, and (ii) allow for sliding movement of said strand of suture relative to said connector portion of said suture anchor once said suture anchor has been installed in said bone.

5. A suture anchor according to claim 1 wherein said head portion and said connector portion comprise a unitary construction.

6. A suture anchor according to claim 5 wherein said suture anchor is adapted to be in threaded engagement with bone when said suture anchor is deployed in said bone.

7. A suture anchor according to claim 1 wherein said connector portion in cross-section is hexagonal.

* * * * *